(12) United States Patent
Jack et al.

(10) Patent No.: US 10,416,109 B2
(45) Date of Patent: Sep. 17, 2019

(54) MICROCHIP STRUCTURE AND TREATMENTS FOR ELECTROCHEMICAL DETECTION

(71) Applicant: General Atomics, San Diego, CA (US)

(72) Inventors: Graham D. Jack, Toronto (CA); Ryan B. Hayman, Toronto (CA)

(73) Assignee: General Atomics, San Diego, CA (US)

( * ) Notice: Subject to any disclaimer, the term of this patent is extended or adjusted under 35 U.S.C. 154(b) by 361 days.

(21) Appl. No.: 14/454,659

(22) Filed: Aug. 7, 2014

(65) Prior Publication Data

US 2015/0041315 A1 Feb. 12, 2015

Related U.S. Application Data

(60) Provisional application No. 61/863,398, filed on Aug. 7, 2013.

(51) Int. Cl.
*G01N 27/327* (2006.01)
*B81B 1/00* (2006.01)
*B81C 1/00* (2006.01)

(52) U.S. Cl.
CPC ......... *G01N 27/327* (2013.01); *B81B 1/006* (2013.01); *B81C 1/00206* (2013.01); *B81C 1/00341* (2013.01)

(58) Field of Classification Search
CPC ............... G01N 33/5438; G01N 27/30; G01N 27/3275; G01N 27/3278; G01N 37/3272; G01N 27/403; G01N 27/416; G01N 27/27; G01N 27/327; B81C 1/00206; B81C 1/00341; B81B 1/006; Y10S 977/754; Y10S 977/925; C12Q 1/6825; C12Q 1/6876; C12Q 1/001; C12Q 2563/137; C12Q 2565/607

See application file for complete search history.

(56) References Cited

U.S. PATENT DOCUMENTS

| | | | |
|---|---|---|---|
| 2004/0055901 A1 | 3/2004 | Petersen et al. | |
| 2007/0105210 A1 | 5/2007 | Delattre et al. | |
| 2007/0207055 A1 | 9/2007 | Marchand et al. | |
| 2008/0308418 A1 | 12/2008 | Dipiazza et al. | |
| 2013/0244340 A1* | 9/2013 | Davis | G01N 33/48721 436/501 |
| 2013/0316340 A1* | 11/2013 | Kelley | C12Q 1/6825 435/6.11 |

(Continued)

FOREIGN PATENT DOCUMENTS

| | | |
|---|---|---|
| CA | 2735735 | 3/2010 |
| CN | 102216762 A | 10/2011 |
| EP | 0243278 | 10/1987 |

(Continued)

OTHER PUBLICATIONS

PCT International Search Report and Written Opinion of the International Searching Authority of Application No. PCT/IB2014/002448, dated Mar. 19, 2015 (9 pages).

(Continued)

*Primary Examiner* — Xiuyu Tai

(57) ABSTRACT

Disclosed herein are processes and devices for use in the electrochemical detection of a target in a sample. For example, silicon or glass surfaces are treated with silanes functionalized with various side chains to tune the surface wetting characteristics.

20 Claims, 5 Drawing Sheets

(56) References Cited

U.S. PATENT DOCUMENTS

2014/0020936 A1* 1/2014 Kim ................. H05K 1/02
174/255

FOREIGN PATENT DOCUMENTS

| WO | WO 2010/025547 A1 | 3/2010 |
| WO | WO-2011022173 | 2/2011 |
| WO | WO 2012/097081 A2 | 7/2012 |

OTHER PUBLICATIONS

Arkles, B., "Tailoring surfaces with silanes," Chemtech, vol. 7, pp. 766-778, 1977.
Desbief, S. et al., "Impact of chain length, temperature, and humidity on the growth of long alkyltrichlorosilane self-assembled monolayers," Phys. Chem. Phys., vol. 13, No. 7, pp. 2870-2879, 2011.
Extended European Search Report dated Jun. 29, 2017 for European Application No. 14834423.7, 10 pages.
Office Action dated Jan. 24, 2017 for Chinese Application No. 201480055259.4, with English translation, 12 pages.
Soleymani, L. et al., "Nanostructuring of Patterned Microelectrodes to Enhance the Sensitivity of Electrochemical Nucleic Acids Detection," Angewandte Chemie, vol. 48, No. 45, pp. 8457-8460, 2009.
Sung, M. M. et al., "Formation of alkylsiloxane self-assembled monolayers in $Si_3N_4$," J. Vac. Sci. Technol. A, vol. 17, No. 2, pp. 540-544, 1999.
Extended European Search Report dated May 13, 2019 for European Application No. 14834423.7, 8 pages.

* cited by examiner

MICROCHIP STRUCTURE AND TREATMENTS FOR ELECTROCHEMICAL DETECTION

CROSS-REFERENCE TO RELATED APPLICATION

This application claims priority to U.S. Provisional Application No. 61/863,398 filed Aug. 7, 2013, which is hereby incorporated by reference herein in its entirety.

BACKGROUND

The use of capture probes attached to a substrate within an electrochemical biosensing device, such as a nanostructured microelectrode (NME), for biomarker analysis is known in the art. As the probe captures its negatively charged target it causes increased negative charge near the surface of the electrode which can be detected electrochemically by an increase in current as a potential is applied. The NME is typically electrochemically plated onto patterned gold electrodes on a glass or semi-conducting substrate, such as silicon. Silicon or glass wafer lithographic methods which often involve silicon dioxide ($SiO_2$) or silicon nitride ($Si_3N_4$), layer deposition and patterning are well developed for the electronics industry but these substrates are not typically designed for exposure to solutions, a common practice in electrochemical sensing applications. Dioxide layers tend to be more porous, which may cause biomolecule adsorption or trapping, which in turn poses problems with the detection of targets. Further, penetration of the electrolyte solution to underlying layers of the substrate may have undesirable effects during electrochemical sensing. The isoelectric points of silicon dioxide (pH1.7-3.5) and silicon nitride (pH9) are significantly different from each other and from the solutions used during electrochemical sensing. Additionally, the fabrication, dicing, and etching processes used to create silicon or glass chips suitable for NME growth sometimes leave surface contaminants or residues that affect the water contact angle. This effect results in variable surface wetting that has downstream effects in sensor fabrication, probe deposition, the assay, and microfluidic cassette functionality. There is therefore a need for silicon or glass substrates with chemical surface modification that can be utilized in procedures involving wet chemistry and biosensing that addresses the aforementioned problems. There is also a need for a consistent hydrophobic surface, which prevents wicking effects and spreading of solutions which can occur when depositing multiple probe-containing droplets on a single chip to functionalize individual NMEs with unique probes.

SUMMARY

Disclosed herein are processes and devices for use in the electrochemical detection of a target in a sample.

According to an aspect, there is provided a process for the manufacture of a biosensing device, the process comprising the steps of;
(i) providing a substrate having an electrically conductive lead on a surface thereof;
(ii) applying an insulating layer to the substrate and the lead, said insulating layer comprising one or more of silicon dioxide or silicon nitride;
(iii) etching an aperture in the insulating layer to expose a portion of the lead onto which a nanostructured microelectrode is to be plated;
(iv) oxidizing one or more of the silicon dioxide or silicone nitride to form oxidized silicon dioxide or silicone nitride, and;
(v) allowing one or more of the oxidized silicon dioxide or silicon nitride to react with a functionalized silane.

According to another aspect, there is provided a process for the manufacture of a biosensing device, the process comprising the steps of;
(i) providing a substrate having an electrically conductive lead on a surface thereof;
(ii) applying an insulating layer to the substrate and the lead, said insulating layer comprising one or more of silicon dioxide or silicon nitride;
(iii) etching an aperture in the insulating layer to expose a portion of the lead onto which a nanostructured microelectrode is to be plated;
(iv) etching the surface to clean and/or oxidize the surface, and;
(v) allowing the etched surface to react with a functionalized silane.

According to a further aspect, there is provided a biosensing device manufactured according to the processes herein described.

According to a further aspect, there is provided the use of a functionalized silane to modify the hydrophobicity of a silicon dioxide or silicon nitride surface.

DETAILED DESCRIPTION

Figure 1:
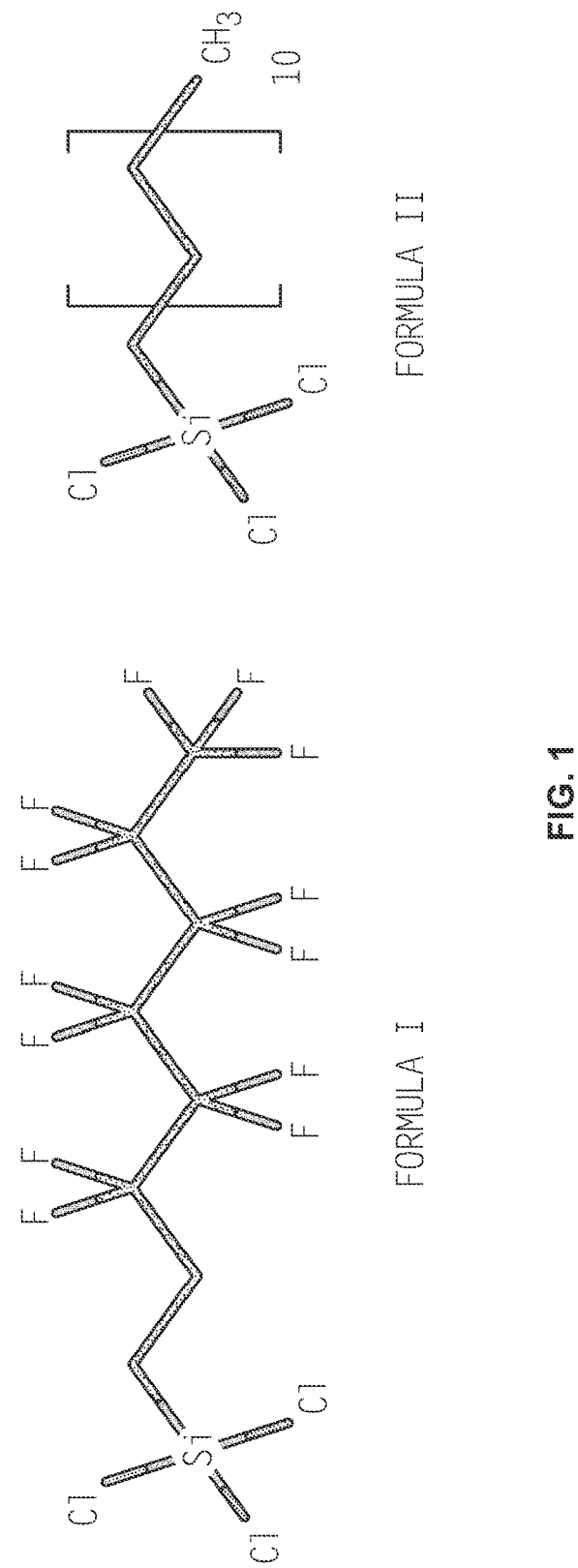
FIG. 1 illustrates examples of suitable trichlorosilanes for use in the process according to some implementations.

To provide an overall understanding of the systems, devices, and methods described herein, certain illustrative embodiments will be described. It is to be understood that the systems, devices, and methods disclosed herein, while shown for use in diagnostic systems for bacterial infections such as *Chlamydia*, may be applied in other applications including, but not limited to, detection of other bacteria, viruses, fungi, prions, plant matter, animal matter, protein, RNA sequences, DNA sequences, as well as cancer screening and genetic testing, including screening for genetic traits and disorders.

During substrate layup, a layer of silicon dioxide ($SiO_2$) or silicon nitride ($Si_3N_4$) is grown on the surface of the chip using methods known in the art. As noted above, these materials have characteristics that may require further optimization for application in wet chemistry and biosensing. In one implementation, the chip surface includes a layer of silicon dioxide and a layer of silicon nitride. Preferably, the layer of silicon dioxide is disposed on the chip between the chip surface and the silicon nitride layer, such that the silicon nitride layer is disposed on top of the silicon dioxide layer. Use of a silicon nitride layer on top of the usually porous silicon dioxide layer decreases the binding of biomolecules and caps defects (i.e., pores) that would cause the growth of spurious gold structures during NME plating.

In addition, the fabrication, dicing, and etching processes used to create silicon chips suitable for NME growth sometimes leave surface contaminants or residues that affect the water contact angle. This effect results in variable surface wetting that has downstream effects in sensor fabrication, probe deposition, the assay, and microfluidic cassette function. According to some embodiments, the silicon or glass surfaces are treated with silanes functionalized with various side chains to tune the surface wetting characteristics. Capping the insulating layer of the chip with this self-assembled monolayer (SAM) of silanes isolates the chip surface from the sample and electrochemical solutions by controlling the wetting of the surface. The SAM decreases surface energy, increases surface contact angle with the water, and decreases surface variability created during chip manufacturing that have downstream sensing effects. This procedure typically involves oxidation of the surface and exposure to reactive silanes under vacuum. Exposure of silicon dioxide and silicon nitride to oxygen plasma for several minutes removes contaminants and oxidizes the silicon or glass surface, activating the substrate for subsequent silanization. Only the oxidized silicon reacts with the silane molecules, leaving any exposed gold surfaces (now cleaned by oxygen plasma) unaffected and prepared for NME plating. In the presence of trace surface water, the chlorines are eliminated in the form of hydrochloric acid to form a silanol intermediate, which then reacts with surface hydroxyl groups and neighboring silanol molecules to form a network.

FIG. 1 illustrates non-limiting examples of suitable tricholorosilanes for functionalization of silicon dioxide or silicon nitride. The compound of Formula I is trichloro(1H, 1H, 2H, 2H-perfluorooctyl)silane. The compound of Formula II is tricholorododecylsilane. In further implementations, other tricholorosilanes having a functionalized alkyl side chain may be utilized.

Figure 2:
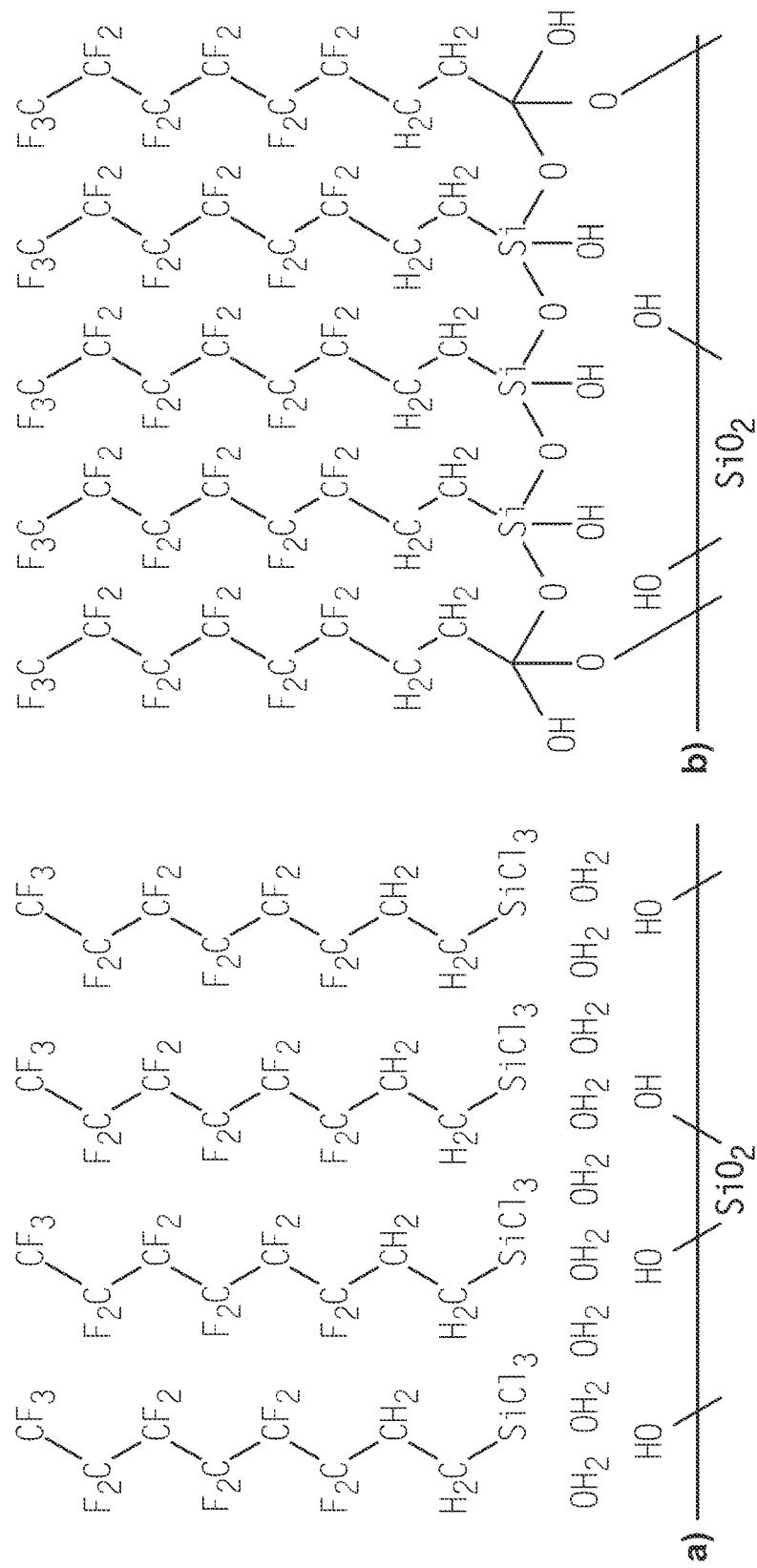
FIG. 2 illustrates a schematic of a self-assembled monolayer (SAM) forming on a silicon dioxide surface using trichloro(1H, 1H, 2H, 2H-perfluorooctyl)silane according to some implementations.

FIG. 2 illustrates the formation of a self-assembled monolayer (SAM) using the compound of Formula I onto the silicon dioxide surface according to some implementations. Panel (a), demonstrates the compound of Formula I being brought within proximity of the surface hydroxyl groups of the oxidized silicon dioxide surface. As demonstrated in Panel (b), in the presence of trace surface water on the silicon dioxide surface, the chlorines are eliminated in the form of hydrochloric acid to form a silanol intermediate molecule. This intermediate then reacts with the surface hydroxyl groups and any neighboring silanol intermediate molecules to form a self-assembling network which provides a hydrophobic coating to the surface. Only the oxidized silicon reacts with the silanes and the other components of the device, for example, the exposed electrically conductive lead onto which the nanostructured microelectrode is to be deposited, remain un-modified by this chemical modification.

A consistent hydrophobic surface has several advantages in NME sensor production and assay. For example, controlling the wetting and subsequent spread of solutions on the surface prevents undesired interactions with electrical contacts and interfaces to the instrument circuits. Isolation of the electrical contacts from solutions also insures that the NME channels are kept separate during the sensing operations. Controlled wetting of these hydrophobic surfaces permits the use of precision fluidic handling and probe deposition by mechanical spotters. By keeping drops discrete and separated, multiple probe sequences can be deposited on neighboring NMEs with minimal spacing required.

A biosensing device can be produced as follows. In some implementations, the device may include a substrate of glass or silicon with a single electrically conductive lead, which can serve as a working electrode for growing a single NME. The device may also include a counter electrode and a reference electrode, either separate from the substrate or lithographically patterned onto the substrate. In some implementations, multiple electrically conductive leads may be included on the substrate to produce a multiplexed biosensing device. In such cases, each electrically conductive lead can serve as a working electrode for growing one or more NMEs. In some implementations, each working electrode may have its own corresponding counter electrode and reference electrode. In some implementations, a single counter electrode may be shared by some or all of the working electrodes. The working, counter, and reference electrodes may be lithographically patterned to be housed within various layers of the device. For example, the working electrode can be affixed to a silicon or glass substrate and partially covered with an insulating layer. The reference and counter electrodes can be deposited on top of the insulating layer.

In certain implementations, some or all of the electrically conductive leads are covered by an insulating layer, such as silicon dioxide or silicon nitride. Etching techniques, by wet chemical or reactive ion methods, are used to selectively expose portions of the leads, and the exposed portions can serve as working electrodes for electrochemical detection or sites for NME growth. The insulating layer is then oxidized and allowed to react with a functionalized silane according to the methods described herein. The silane molecules only form covalent bonds with the oxidized portions of the insulator, while avoiding the metallic components. In certain implementations that involve counter and reference electrodes patterned on top of the insulator, these components will be unaffected by the silane layer. NMEs can then be plated on the apertures of the device. Functionalization of the NMEs can be accomplished, for example, by depositing discrete probe-containing droplets onto the device with specific nucleotide sequences. The hydrophobicity of the silane layer prevents spreading of the droplet, which in turn prevents undesired mixing of probe sequences.

Figure 3:
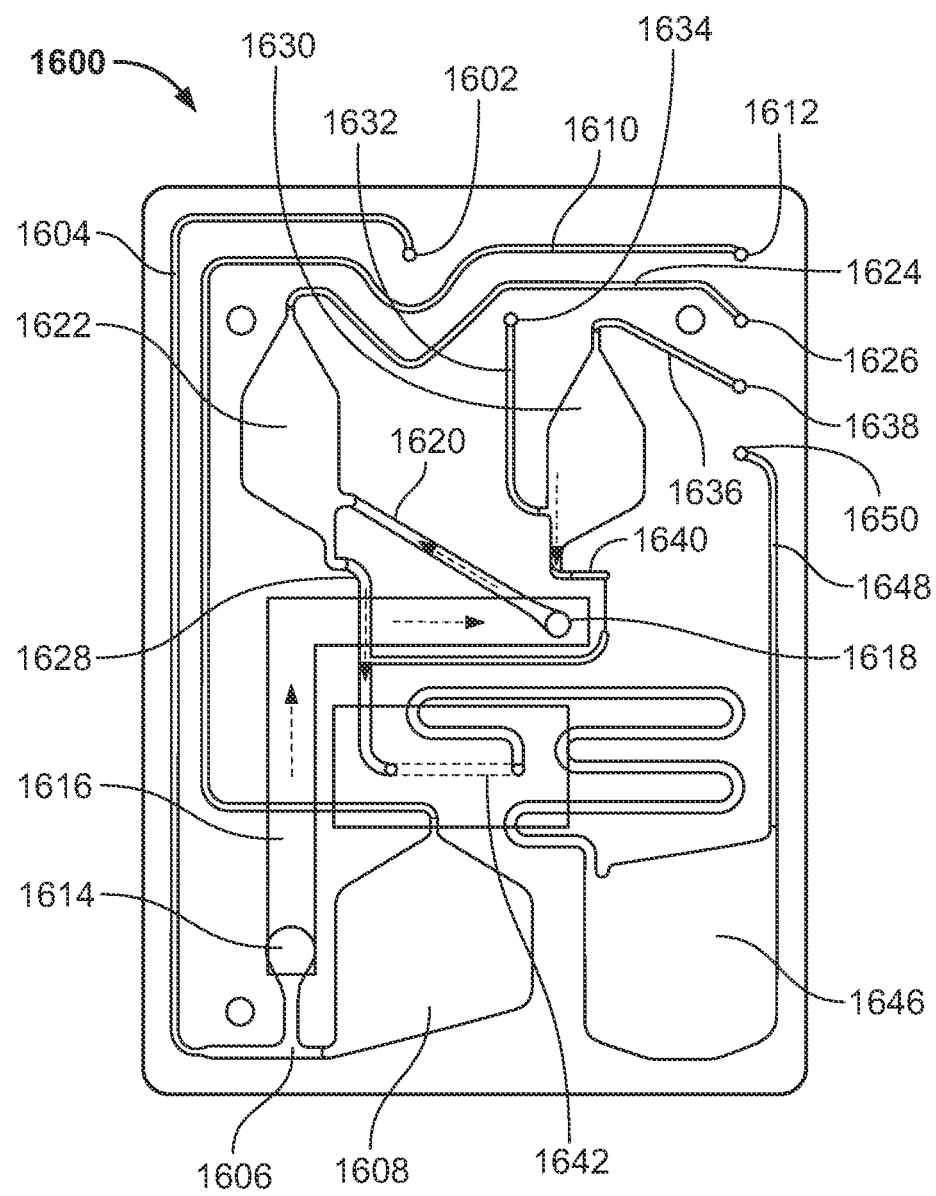
FIG. 3 depicts a cartridge system for receiving, preparing, and analyzing a biological sample utilizing a probe attached to a biosensing device as herein described.

The biosensing device as described herein is used in a system 1600, illustrated in FIG. 3 which includes ports, channels, and chambers. System 1600 may transport a sample through the channels and chambers by applying fluid pressure, for example, with a pump or pressurized gas or liquids. In certain embodiments, ports 1602, 1612, 1626, 1634, 1638, and 1650 may be opened and closed to direct fluid flow. In use, a sample is collected from a patient and applied to the chamber through port 1602. In certain approaches, the sample is collected into a chamber or test tube, which connects to port 1602. In practice, the sample is a fluid, or fluid is added to the sample to form a sample solution. In certain approaches, additional reagents are added to the sample. The sample solution is directed through channel 1604, past sample inlet 1606, and into degassing chamber 1608 by applying fluid pressure to the sample through port 1602 while opening port 1612 and closing ports 1626, 1634, 1638, and 1650. The sample solution enters and collects in degassing chamber 1608. Gas or bubbles from the sample solution also collect in the chamber and are expelled through channel 1610 and port 1612. If bubbles are not removed, they may interfere with processing and analyzing the sample, for example, by blocking flow of the sample solution or preventing the solution from reaching parts of the system, such as a lysis chamber or sensor. In certain embodiments, channel 1610 and port 1612 are elevated higher than degassing chamber 1608 so that the gas rises into channel 1610 as chamber 1608 is filled. In certain approaches, a portion of the sample solution is pumped through channel 1610 and port 1612 to ensure that all gas has been removed.

After degassing, the sample solution is directed into lysis chamber 1616 by closing ports 1602, 1634, 1638, and 1650, opening port 1626, and applying fluid pressure through port 1612. The sample solution flows through inlet 1606 and into lysis chamber 1616. In certain approaches, system 1600 includes a filter 1614. Filter 1614 may be a physical filter, such as a membrane, mesh, or other material to remove materials from the sample solution, such as large pieces of tissue, which could clog the flow of the sample solution through system 1600. Lysis chamber 1616 may be similar to lysis chamber 1200 or lysis chamber 1310 described previously. When the sample is in lysis chamber 1616, a lysis procedure, such as an electrical or chemical procedure as described above, may be applied to release analytes into the sample solution. For example, the lysis procedure may rupture cells to release nucleic acids, proteins, or other molecules which may be used as markers for a pathogen, disease, or host. In certain approaches, the sample solution flows continuously through lysis chamber 1616. Additionally or alternatively, the sample solution may be agitated while in lysis chamber 1616 before, during, or after the lysis procedure. Additionally or alternatively, the sample solution may rest in lysis chamber 1616 before, during, or after the lysis procedure.

Electrical and/or chemical lysis procedures may produce gases (e.g., oxygen, hydrogen), which form bubbles. Bubbles formed from lysis or agitation of solutions with surfactants may interfere with other parts of the system. For example, they may block flow of the sample solution or interfere with the capture and sensing of the marker at the probe and sensor. Accordingly, the sample solution is directed to a degassing chamber or bubble trap 1622. The sample solution is directed from lysis chamber 1616 through opening 1618, through channel 1620, and into bubble trap 1622 by applying fluid pressure to the sample solution through port 1612, while keeping port 1626 open and ports 1602, 1634, 1638, and 1650 closed. Similar to degassing chamber 1608, the sample solution flows into bubble trap 1622 and the gas or bubbles collect and are expelled through channel 1624 and port 1626. For example, channel 1624 and port 1626 may be higher than bubble trap 1622 so that the gas rises into channel 1624 as bubble trap 1622 is filled. In certain approaches, a portion of the sample solution is pumped through channel 1624 and port 1626 to ensure that all gas has been removed.

After removing the bubbles, the sample solution is pumped through channel 1628 and into analysis chamber 1642 by applying fluid pressure through port 1626 while opening port 1650 and closing ports 1602, 1612, 1634, and 1638. Analysis chamber 1642 includes probes, such as a pathogen probe, host probe, and non-sense probe. In certain approaches, the sample solution flows continuously through analysis chamber 1642. Additionally or alternatively, the sample solution may be agitated while in analysis chamber 1642 to improve capture of the targets with the probes on the sensors. In certain approaches, system 1600 includes a fluid delay line 1644, which provides a holding space for portions of the sample during capture and agitation. In certain approaches, the sample solution sits idle while in analysis chamber 1642 as a delay to allow capture.

System 1600 includes a regent chamber 1630, which holds electrocatalytic reagents, such as transition metal complexes $Ru(NH_3)_6^{3+}$ and $Fe(CN)_6^{3-}$, for electrocatalytic detection of markers in the sample solution. In certain approaches, the electrocatalytic reagents are stored in dry form with a separate rehydration buffer. For example, the rehydration buffer may be stored in a foil pouch above rehydration chamber 1630. The pouch may be broken or otherwise opened to rehydrate the reagents. In certain approaches, a rehydration buffer may be pumped into rehydration chamber 1630. Adding the buffer may introduce bubbles into chamber 1630. Gas or bubbles may be removed from rehydration chamber 1630 by applying fluid pressure through port 1638, while opening port 1634 and closing ports 1602, 1624, 1626, and 1650 so that gas is expelled through channel 1630 and port 1634. Similarly, fluid pressure may be applied through port 1634 while opening port 1638. After the sample solution has had sufficient time to allow the markers to be captured by the sensor probes in the analysis chamber, the hydrated and degassed reagent solution is pumped through channel 1640 and into analysis chamber 1642 by applying fluid pressure through port 1638, while opening port 1650 and closing all other ports. The reagent solution pushes the sample solution out of analysis chamber 1642, through delay line 1644, and into waste chamber 1646 leaving behind only those molecules or markers which have been captured by the probes of the sensors in analysis chamber 1642. In certain approaches, the sample solution may be removed from the cartridge system 1600 through channel 1648, or otherwise further processed. The reagent solution fills analysis chamber 1642. In certain approaches, the reagent solution is mixed with the sample solution before the sample solution is moved into analysis chamber 1642, or during the flow of the sample solution into analysis chamber 1642. After the reagent solution has been added, an electrocatalytic analysis procedure to detect the presence or absence of markers is performed as previously described.

Figure 4:
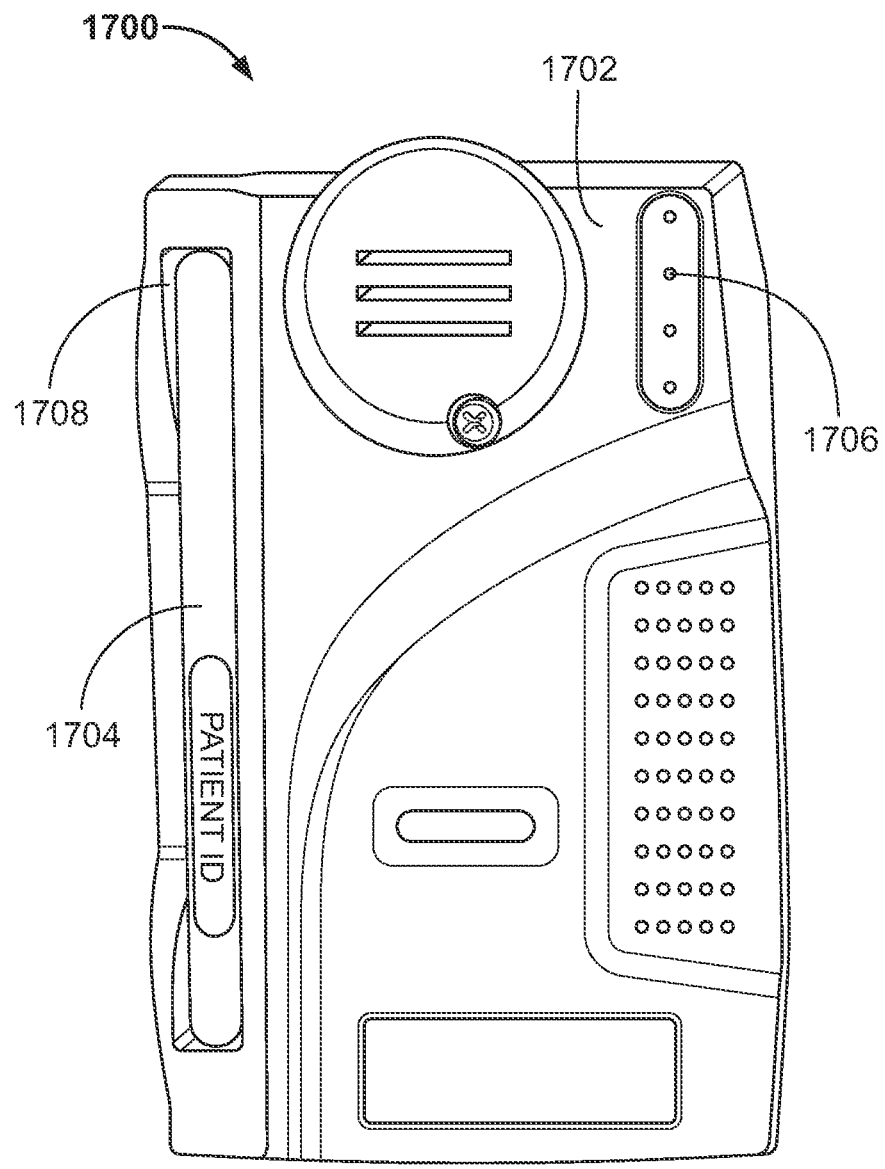
FIG. 4 depicts a cartridge for an analytical detection system according to some implementations.
Figure 5:
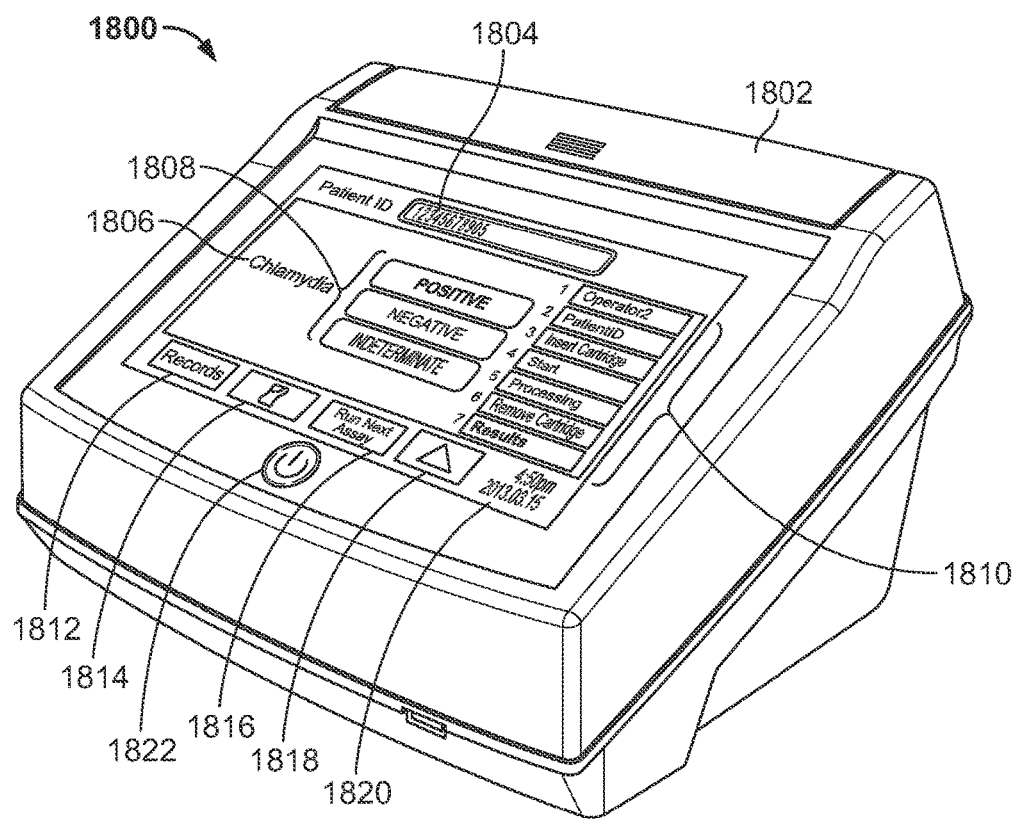
FIG. 5 depicts an automated testing system according to some implementations.

FIG. 4 depicts an embodiment of a cartridge for an analytical detection system. Cartridge 1700 includes an outer housing 1702, for retaining a processing and analysis system, such as system 1600. Cartridge 1700 allows the internal processing and analysis system to integrate with other instrumentation. Cartridge 1700 includes a receptacle 1708 for receiving a sample container 1704. A sample is received from a patient, for example, with a swab. The swab is then placed into container 1704. Container 1704 is then positioned within receptacle 1708. Receptacle 1708 retains the container and allows the sample to be processed in the analysis system. In certain approaches, receptacle 1708 couples container 1704 to port 1602 so that the sample can be directed from container 1704 and processed though system 1600. Cartridge 1700 may also include additional features, such as ports 1706, for ease of processing the sample. In certain approaches, ports 1706 correspond to ports of system 1600, such as ports 1602, 1612, 1626, 1634, 1638, and 1650 to open or close to ports or apply pressure for moving the sample through system 1600.

Cartridges may use any appropriate formats, materials, and size scales for sample preparation and sample analysis. In certain approaches, cartridges use microfluidic channels and chambers. In certain approaches, the cartridges use macrofluidic channels and chambers. Cartridges may be single layer devices or multilayer devices. Methods of fabrication include, but are not limited to, photolithography, machining, micromachining, molding, and embossing.

FIG. 4 depicts an automated testing system to provide ease of processing and analyzing a sample. System 1800 may include a cartridge receiver 1802 for receiving a cartridge, such as cartridge 1700. System 1800 may include other buttons, controls, and indicators. For example, indicator 1804 is a patient ID indicator, which may be typed in manually by a user, or read automatically from cartridge 1700 or cartridge container 1704. System 1800 may include a "Records" button 1812 to allow a user to access or record relevant patient record information, "Print" button 1814 to print results, "Run Next Assay" button 1818 to start processing an assay, "Selector" button 1818 to select process steps or otherwise control system 1800, and "Power" button 1822 to turn the system on or off. Other buttons and controls may also be provided to assist in using system 1800. System 1800 may include process indicators 1810 to provide instructions or to indicate progress of the sample analysis. System 1800 includes a test type indicator 1806 and results indicator 1808. For example, system 1800 is currently testing for *Chlamydia* as shown by indicator 1806, and the test has resulted in a positive result, as shown by indicator 1808. System 1800 may include other indicators as appropriate, such as time and date indicator 1820 to improve system functionality.

The foregoing is merely illustrative of the principles of the disclosure, and the systems, devices, and methods can be practiced by other than the described embodiments, which are presented for the purposes of illustration and not of limitation. It is to be understood that the systems, devices, and methods disclosed herein, while shown for use in detection systems for bacteria, and specifically, for *Chlamydia trachomatis*, may be applied to systems, devices, and methods to be used in other applications including, but not limited to, detection of other bacteria, viruses, fungi, prions, plant matter, animal matter, protein, RNA sequences, DNA sequences, as well as cancer screening and genetic testing, including screening for genetic disorders.

Variations and modifications will occur to those of skill in the art after reviewing this disclosure. The disclosed features may be implemented, in any combination and sub-combination (including multiple dependent combinations and sub-combinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited are hereby incorporated by reference herein in their entireties and made part of this application.

The invention claimed is:

1. A process for the manufacture of a biosensing device, the process comprising:
providing a substrate having an electrically conductive lead on a surface thereof;
applying an insulating layer to the substrate and the electrically conductive lead, said insulating layer comprising one or more of silicon dioxide and silicon nitride;
etching an aperture in the insulating layer to expose a portion of the electrically conductive lead onto which a nanostructured microelectrode is to be plated;
oxidizing one or more of the silicon dioxide and the silicon nitride to form oxidized silicon dioxide or oxidized silicon nitride;
allowing one or more of the oxidized silicon dioxide and the oxidized silicon nitride to react with a functionalized silane; and
forming a self-assembled monolayer of the functionalized silane on the insulating layer.

2. The process of claim 1, wherein the insulating layer comprises a layer of silicon dioxide and a layer of silicon nitride.

3. The process of claim 2, wherein the layer of silicon dioxide is disposed between the substrate and the layer of silicon nitride.

4. The process of claim 1, wherein the step of oxidizing one or more of the silicon dioxide and the silicon nitride occurs at a top surface of the insulating layer.

5. The process of claim 1, wherein the step of oxidizing one or more of the silicon dioxide and the silicon nitride forms a deactivated oxidized silicon dioxide or a deactivated oxidized silicon nitride.

6. The process of claim 1, wherein a plurality of insulating layers is applied to the substrate.

7. The process of claim 1, wherein the aperture is etched through the insulating layer.

8. The process of claim 1, wherein allowing one or more of the oxidized silicon dioxide and the oxidized silicon nitride to react with the functionalized silane includes applying a vacuum.

9. The process of claim 1, wherein the self-assembled monolayer of a functionalized silane provides a hydrophobic coating.

10. A process for the manufacture of a biosensing device, the process comprising:
providing a substrate having an electrically conductive lead on a surface thereof;
applying an insulating layer to the substrate and the electrically conductive lead, said insulating layer comprising one or more of silicon dioxide and silicon nitride;
etching an aperture in the insulating layer to expose a portion of the electrically conductive lead onto which a nanostructured microelectrode is to be plated;
etching a surface of the insulating layer and a surface of the electrically conductive lead to clean and/or oxidize the surfaces; and
capping the etched surface of the insulating layer with a self-assembled monolayer of functionalized silane.

11. The process of claim 10, wherein a plurality of insulating layers is applied to the substrate.

12. The process of claim 11, wherein the aperture is etched through an insulating layer.

13. The process of claim 10, wherein etching the surface comprises subjecting the surface to plasma etching.

14. The process of claim 10, wherein the functionalized silane is a trichlorosilane.

15. The process of claim 14, wherein the trichlorosilane has a functionalized alkyl side chain.

16. The process of claim 15, wherein the trichlorosilane is trichloro(1H, 1H, 2H, 2H-perfluorooctyl) silane or trichlorododecylsilane.

17. The process of claim 10, wherein oxidizing the surface occurs during exposure to oxygen plasma.

18. The process of claim 10, further comprising: plating the nanostructured microelectrode in the aperture.

19. The process of claim 10, wherein capping the etched surface of the insulating layer with the self-assembled monolayer of functionalized silane includes reacting the functionalized silane under a vacuum with an oxidized surface of the insulating layer.

20. The process of claim 10, wherein the self-assembled monolayer of a functionalized silane provides a hydrophobic coating.

\* \* \* \* \*